(12) United States Patent
Mirejovsky

(10) Patent No.: US 6,709,674 B2
(45) Date of Patent: Mar. 23, 2004

(54) INJECTABLE PAMIDRONATE DISODIUM

(75) Inventor: Dorla Mirejovsky, Irvine, CA (US)

(73) Assignee: Gensia Sicor Pharmaceuticals, Inc., Irvine, CA (US)

(*) Notice: Subject to any disclaimer, the term of this patent is extended or adjusted under 35 U.S.C. 154(b) by 81 days.

(21) Appl. No.: 10/137,205

(22) Filed: May 1, 2002

(65) Prior Publication Data

US 2003/0069211 A1 Apr. 10, 2003

Related U.S. Application Data

(60) Provisional application No. 60/288,293, filed on May 2, 2001.

(51) Int. Cl.[7] ................................. A61K 9/48
(52) U.S. Cl. ...................... 424/451; 424/400; 424/452; 424/422
(58) Field of Search .............................. 424/451, 452, 424/400, 422

(56) References Cited

U.S. PATENT DOCUMENTS

| 3,962,432 A | * | 6/1976 | Schmidt-Dunker ......... 424/204 |
| 4,711,880 A | | 12/1987 | Stahl et al. |
| 6,160,165 A | | 12/2000 | Shinal |
| 6,268,524 B1 | | 7/2001 | Shinal |
| 2002/0058647 A1 | | 5/2002 | Handreck et al. |

OTHER PUBLICATIONS

Physician's Desk Reference 2000, pp. 1998–2003.

* cited by examiner

*Primary Examiner*—Thurman K. Page
*Assistant Examiner*—S. Howard

(57) ABSTRACT

The invention includes a packaged liquid composition of a pamidronate alkaline salt in a sealed storage vessel having an inner surface which is non-reactive with the pamidronate alkaline salt composition.

19 Claims, No Drawings

INJECTABLE PAMIDRONATE DISODIUM

This application claims priority to U.S. Provisional Application Ser. No. 60/288,293, filed May 2, 2001, the entire disclosure of which is hereby incorporated by reference.

FIELD OF THE INVENTION

This invention relates to storage stable injectable pamidronate alkaline salt solutions. The invention also relates to the preparation and use of these solutions in non-reactive containers.

BACKGROUND AND INTRODUCTION TO THE INVENTION

Pamidronate disodium, also known as disodium 3-amino-1-hydroxypropane-1,1-diphosphonate (I), is used in the treatment of diseases associated with calcium and/or

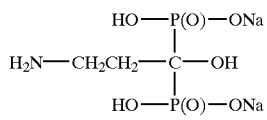

phosphate metabolism. Schmidt-Dünker, U.S. Pat. No. 3,962,432, disclosed that aminoalkane-diphosphonic acids or their water-soluble salts are suitable for the therapeutic treatment of disorders associated with abnormal deposition of calcium salts, including inflammatory diseases, arteriosclerosis and osteoporosis.

Novartis Pharmaceutical Corp. currently markets Aredia®, a lyophilized pamidronate disodium pentahydrate, which is used to inhibit bone resorption and to treat hypercalcemia, as well as to treat metastatic bone pain. The Physicians Desk Reference 2000 reports that Aredia®, when reconstituted with Sterile Water for Injection, is capable of being stored under refrigeration for up to 24 hours. Stahl et al., U.S. Pat. No. 4,711,880, disclosed a crystalline form of pamidronate disodium and a pharmaceutical preparation intended for enteral administration containing the crystalline salt.

SUMMARY OF THE INVENTION

This invention is directed towards a storage stable liquid pamidronate alkaline salt composition in a sealed storage vessel having an inner surface which is non-reactive with the pamidronate alkaline salt composition. The pamidronate alkaline salt may be, for example, pamidronate disodium or pamidronate dipotassium.

In one embodiment, the invention is directed to a packaged composition of a pamidronate alkaline salt in a sealed storage vessel. The pamidronate salt composition comprises a pamidronate alkaline salt, water, a sugar, a pharmaceutically acceptable base, and a pharmaceutically acceptable acid. The inner surface of the sealed storage vessel may be made of any material which is non-reactive with the pamidronate alkaline salt composition.

In another embodiment, the invention is directed to a method for preparing a packaged pamidronate alkaline salt composition by (a) combining a sugar with water; (b) combining the mixture of step (a) with pamidronic acid to form a pamidronic acid slurry; (c) adding to the pamidronic acid slurry sufficient aqueous solution of sodium hydroxide or potassium hydroxide to yield a solution having a pH of about 8.5; (d) adding to the resultant solution a pharmaceutically acceptable acid in an amount sufficient to lower the pH of the solution to about 6.5; (e) transferring the solution having a pH of about 6.5 into a vessel having an inner surface which does not react with the solution; and (f) sealing the vessel.

DETAILED DESCRIPTION OF THE INVENTION

The present invention is based on the discovery that storage vessels made of glass may react with the pamidronate alkaline salt compositions. It is believed that glass may leach calcium or silicate which may react with pamidronate salt and thereby inhibit its therapeutic effectiveness. The present invention is directed to a storage stable liquid composition of a pamidronate alkaline salt in a sealed storage vessel having an inner surface which is non-reactive with the pamidronate salt composition. Thus, the inner surface of the storage vessel is made of a material other than glass.

In one embodiment, the invention is directed to a packaged composition of a pamidronate alkaline salt in a sealed storage vessel. The pamidronate salt composition comprises a pamidronate alkaline salt, water, a sugar, a pharmaceutically acceptable base, and a pharmaceutically acceptable acid. The inner surface of the sealed storage vessel may be made of any material which is non-reactive with the pamidronate alkaline salt composition. The pamidronate alkaline salt may be, for example, pamidronate disodium or pamidronate dipotassium.

Typically, the sealed storage vessel is a vial. In one embodiment, the inner surface of the sealed storage vessel is made of plastic. For example, the inner surface of the sealed storage vessel may be made of polypropylene. Another type of non-glass vials, Resin CZ® vials, is available from West Pharmaceutical Services (Lionville, Pa.).

Sugars, which may be used in the pamidronate alkaline salt compositions of the present invention, include mannitol, lactose and sucrose. Typically, the sugar is mannitol.

Pharmaceutically acceptable bases, which may be used in the pamidronate alkaline salt compositions of the present invention, include sodium hydroxide and potassium hydroxide.

Pharmaceutically acceptable acids, which may be used in the pamidronate alkaline salt compositions of the present invention, include phosphoric acid, nitric acid, sulfuric acid, hydrochloric acid, methanesulphonic acid, benzenesulphonoic acid, acetic acid, citric acid, lactic acid, propionic acid, tartaric acid, glutamic acid, maleic acid, ascorbic acid, fumaric acid, succinic acid, methyl sulfuric acid, and benzyl sulfonic acid. Typically, the pharmaceutically acceptable acid is phosphoric acid.

The compositions of the present invention typically have a pH between about 6.0 and about 9.0. Most often, the composition has a pH of about 6.5.

In another embodiment, the invention is directed to a method for preparing a packaged liquid pamidronate alkaline salt composition by (a) combining a sugar with water; (b) combining the mixture of step (a) with pamidronic acid to form a pamidronic acid slurry; (c) adding to the pamidronic acid slurry sufficient aqueous solution of sodium hydroxide or potassium hydroxide to yield a solution having a pH of about 8.5; (d) adding to the resultant solution a pharmaceutically acceptable acid in an amount sufficient to lower the pH of the solution to about 6.5; (e) transferring the solution having a pH of about 6.5 into a vessel having an inner surface which does not react with the solution; and (f) sealing the vessel. Alternatively, a pamidronic acid aqueous slurry can be treated with aqueous sodium hydroxide or potassium hydroxide to form an aqueous solution of pamidronate disodium or pamidronate dipotassium. This solution can then be combined with mannitol and the resulting solution acidified to a pH of about 6.5 with, for example, phosphoric acid.

Sugars, which may be used in the method of this invention, include mannitol, lactose and sucrose. Typically, the sugar is mannitol.

Pharmaceutically acceptable acids, which may be used in the method of this invention, include phosphoric acid, nitric acid, sulfuric acid, hydrochloric acid, methanesulphonic acid, benzenesulphonoic acid, acetic acid, citric acid, lactic acid, propionic acid, tartaric acid, glutamic acid, maleic acid, ascorbic acid, fumaric acid, succinic acid, methyl sulfuric acid, and benzyl sulfonic acid. Typically, the pharmaceutically acceptable acid is phosphoric acid.

The inner surface of the storage vessel used in the method of the present invention may be made of any material which is non-reactive with the pamidronate alkaline salt composition of the invention. For example, the inner surface of the storage vessel may be made of plastic, such as polypropylene.

The pamidronate alkaline salt compositions of the present invention may be useful for treating diseases associated with calcium and/or phosphate metabolism in mammalian, and more preferably, in human patients. The particular carrier employed in these pharmaceutical compositions may vary depending upon the type of administration desired, e.g., enteral, topical or parenteral.

In preparing the pharmaceutical compositions of the present invention in enteral liquid dosage forms (e.g., solutions), typical pharmaceutical media such as water, glycols, oils, alcohols, flavoring agents, preservatives, coloring agents and the like may be employed. For parenteral administration, a carrier will typically comprise sterile water although other ingredients, that aid in solubility or serve as preservatives, may also be included.

The pharmaceutical compositions of the present invention are generally administered in the form of a daily dosage unit at concentrations from about 1 µg/kg of body weight to about 500 mg/kg of body weight. Typically the compositions of the present invention are administered in a daily dosage of from about 10 µg/kg to about 250 mg/kg. Most often the compositions of the present invention are administered in a daily dosage of from about 20 µg/kg to about 100 mg/kg. As recognized by those skilled in the art, the particular quantity of pharmaceutical composition according to the present invention administered to a patient will depend upon a number of factors, including, without limitation, the biological activity desired, the condition of the patient, and tolerance for the drug.

Typically, pamidronate disodium is administered intravenously in dosages of 30 mg, 60 mg or 90 mg over an infusion period of either 4 or 24 hours.

EXAMPLES

The pamidronate disodium solution (3 mg/mL) was prepared by the following steps: Mannitol (470 mg) was added to Water for Injection with stirring. Solid pamidronic acid (25.3 mg) was added with stirring to form a slurry. 1N aqueous sodium hydroxide solution was added, with stirring, until a pH of at least 8.5 was reached and the solution was clear. 1M phosphoric acid was then added to adjust the pH to 6.5. Water for Injection was added to bring the volume total to 10 mL.

Formulation Example 1

An aqueous solution in sealed 10 mL plastic vials, containing a pamidronate disodium concentration of 3 mg/mL and having the following components:

| Pamidronic Acid | 2.53 mg/mL |
| Mannitol | 47.0 mg/mL |
| Water for Injection | q.s. to 10 mL |
| Sodium Hydroxide | adjust pH to at least 8.5 |
| Phosphoric Acid, NF | adjust pH to 6.5 |

Formulation Example 2

An aqueous solution in sealed 10 mL plastic vials, containing a pamidronate disodium concentration of 9 mg/mL and having the following components:

| Pamidronic Acid | 7.59 mg/mL |
| Mannitol | 37.5 mg/mL |
| Water for Injection | q.s. to 10 mL |
| Sodium Hydroxide | adjust pH to at least 8.5 |
| Phosphoric Acid, NF | adjust pH to 6.5 |

While 10 mL vials containing pamidronate disodium compositions containing pamidronate disodium at concentrations of 3 mg/mL and 9 mg/mL have been exemplified, solutions of different volumes and different concentrations of pamidronate disodium may be prepared according to the methods of the present invention.

Example 3

Pamidronate Disodium Injection

Lyophilized pamidronate disodium for injection, 30 mg/vial and 90 mg/vial, is commercially available in glass vials. Pamidronate disodium is a strong chelator and in solution it may extract calcium or silica from glass. Consequently, the reconstituted lyophilized product should be used within 24 hours after reconstitution. It is not expected that the extraction of silica or calcium from glass would be significant within such a short period of time.

Lyophilized pamidronate disodium for injection was reconstituted with water in two glass vials to provide two compositions having pamidronate disodium concentrations of 3 mg/mL and 9 mg/mL, respectively. The data shown in Table 1 demonstrate increasing levels of silicon in the solutions when the reconstituted product was kept in glass vials for an extended period of time. Higher levels of silicon are found in the 9 mg/mL solution than in the 3 mg/mL solution.

TABLE 1

Silicon Levels in Reconstituted Pamidronate Disodium for Injection Stored in Glass Vials at 27.5° C.

| Concentration of Pamidronate Disodium | Silicon/µ/mL | | |
| --- | --- | --- | --- |
| | 2 months | 5 months | 8 months |
| 3 mg/mL | 6.4 | 8.6 | 11.0 |
| 9 mg/mL | 12.4 | 18.3 | 21.6 |

Lyophilized pamidronate disodium for injection was reconstituted with water in two polypropylene vials to provide two compositions having pamidronate disodium concentrations of 3 mg/mL and 9 mg/mL, respectively. The data in Table 2 show that no measurable increase in silicon levels was detected over a period of 12 months for either the 3 mg/mL or the 9 mg/mL solution.

TABLE 2

Silicon Levels in Pamidronate Disodium Injection Stored in Polypropylene Vials at 27.5° C.

| Concentration of Pamidronate Disodium | Silicon/ µ/mL | | | | |
|---|---|---|---|---|---|
| | Zero Time | 3 months | 6 Months | 9 Months | 12 Months |
| 3 mg/mL | <1.8 | <1.8 | <1.8 | <1.8 | <1.8 |
| 9 mg/mL | <1.8 | <1.8 | <1.8 | <1.8 | <1.8 |

The silicon levels were monitored with the ICP method (Inductively Coupled Plasma). The method determines the silicon element that could originate either from silica, silicates, or silicone.

Typically, pharmaceutical manufacturers siliconize the rubber closures. Lubrication of rubber closures with polydimethylsiloxane fluids (PDMS), commonly called silicone oil, is critical to the processability and machinability of stoppers. The level of siliconization is carefully controlled to prevent adsorption of silicone into elastomeric closures, which could leach into the reconstituted product. Such leaching could cause the solution to become hazy, indicating the presence of particulate matter.

Therefore, an additional experiment was performed to demonstrate that silicon levels found in the reconstituted pamidronate disodium for injection in glass vials were caused by the extraction of silica from the glass and not by the extraction of silicone adsorbed to the stoppers. The stoppers used for the lyophilized product typically have a larger product contact area than Teflon-faced stoppers used in the manufacture of pamidronate disodium injection in polypropylene vials.

The stoppers of the lyophilized pamidronate disodium for injection, 30 mg/vial and 90 mg/vial, were removed and the product was reconstituted with 10 mL of Sterile Water for Injection. Then the vials were stoppered using the same Teflon-faced stoppers as used for pamidronate disodium injection in polypropylene vials. Two weeks after the reconstitution the vials were analyzed for silicon content.

The results shown in Table 3 demonstrate that the silicon level in the reconstituted pamidronate disodium for injection, stoppered with the same stoppers as pamidronate disodium injection liquid formulation manufactured in polypropylene vials, exceeds, within 2 weeks, the silicon level found in the liquid product stored in plastic vials for 12 months.

TABLE 3

Silicon Levels in Reconstituted Pamidronate Disodium for Injection in Glass Vials Stoppered with Teflon-Faced Stoppers after Two Weeks at 27.5° C.

| Concentration of Pamidronate Disodium | Silicon/µ/mL 2 Weeks |
|---|---|
| 3 mg/mL | 2.6 |
| 9 mg/mL | 4.9 |

These results support the beneficial use of sealed storage vessels having an inner surface which is non-reactive with pamidronate disodium or pamidronate dipotassium for injection.

While in accordance with the patent statutes, description of the preferred embodiments and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following non-limiting enumerated embodiments.

What is claimed is:

1. A packaged composition comprising:
   (a) an aqueous pamidronate disodium composition comprising:
       (i) disodium pamidronate;
       (ii) a sugar;
       (iii) a pharmaceutically acceptable base; and
       (iv) a pharmaceutically acceptable acid;
       (v) water; and
   (b) a sealed storage vessel having an inner surface which is non-reactive with said pamidronate disodium composition.

2. A packaged composition according to claim 1, wherein said inner surface of said sealed storage vessel is comprised of plastic.

3. A packaged composition according to claim 2, wherein said inner surface of said sealed storage vessel is comprised of polypropylene.

4. A packaged composition according to claim 1, wherein said sugar is selected from the group of mannitol, lactose and sucrose.

5. A packaged composition according to claim 4, wherein said sugar is mannitol.

6. A packaged composition according to claim 5, wherein said pharmaceutically acceptable base is sodium hydroxide.

7. A packaged composition according to claim 6, wherein said pharmaceutically acceptable acid is selected from the group of phosphoric acid, sulfuric acid, hydrochloric acid, acetic acid, methyl sulfuric acid, and benzyl sulfonic acid.

8. A packaged composition according to claim 7, wherein said pharmaceutically acceptable acid is phosphoric acid.

9. A packaged composition according to claim 8, wherein said composition has a pH between about 6.0 and about 9.0.

10. A packaged composition according to claim 9, wherein said composition has a pH of about 6.5.

11. A packaged composition according to claim 1, wherein the concentration of pamidronate salt is from 3 mg/mL to 9 mg/mL.

12. A packaged composition according to claim 11, wherein the pamidronate salt is pamidronate disodium or pamidronate dipotassium.

13. A packaged composition according to claim 12, wherein the pamidronate salt is pamidronate disodium.

14. A method for preparing a packaged aqueous pamidronate disodium composition comprising:
    (a) combining a sugar with water;
    (b) combining the mixture of step (a) with pamidronic acid to form a pamidronic acid slurry;
    (c) adding to said pamidronic acid slurry sufficient aqueous solution of sodium hydroxide to yield a solution having a pH of about 8.5;

(d) adding to the resultant solution a pharmaceutically acceptable acid in an amount sufficient to lower to pH of said solution to about 6.5;

(e) transferring said solution having a pH of about 6.5 into a vessel having an inner surface which does not react with said solution; and (f) sealing said vessel.

15. A method according to claim 14, wherein said sugar is selected from the group of mannitol, lactose and sucrose.

16. A method according to claim 15, wherein said sugar is mannitol.

17. A method according to claim 16, wherein said pharmaceutically acceptable acid is selected from the group of phosphoric acid, sulfuric acid, hydrochloric acid, acetic acid, methyl sulfuric acid, and benzyl sulfonic acid.

18. A method according to claim 17, wherein said acid is phosphoric acid.

19. A method according to claim 18, wherein said inner surface of said storage vessel is comprised of polypropylene.

* * * * *